US005722957A

United States Patent [19]

Steinbach

[11] Patent Number: 5,722,957
[45] Date of Patent: Mar. 3, 1998

[54] IMPLANTABLE INFUSION PUMP

[75] Inventor: Bernd Steinbach, Bad Homburg, Germany

[73] Assignee: Fresenius AG, Germany

[21] Appl. No.: 618,432

[22] Filed: Mar. 15, 1996

[30] Foreign Application Priority Data

Mar. 17, 1995 [DE] Germany ............... 195 09 632.0

[51] Int. Cl.$^6$ ........................... A16M 37/00
[52] U.S. Cl. .............. 604/141; 604/93; 604/131; 604/140
[58] Field of Search ............. 604/93, 131, 132, 604/133, 140, 141, 145–147, 153, 246, 410

[56] References Cited

U.S. PATENT DOCUMENTS

| | | | |
|---|---|---|---|
| 4,714,462 | 12/1987 | DiDomenico | 604/141 |
| 4,784,648 | 11/1988 | Sing et al. | 604/141 |
| 4,902,839 | 2/1990 | Bielefeldt et al. | 570/175 |
| 4,931,050 | 6/1990 | Idriss | 604/141 |
| 4,954,666 | 9/1990 | Bielefeldt et al. | 570/132 |
| 5,207,645 | 5/1993 | Ross et al. | 604/141 |
| 5,242,406 | 9/1993 | Gross et al. | 604/141 |
| 5,382,236 | 1/1995 | Otto et al. | 604/141 |
| 5,514,103 | 5/1996 | Srisathapat et al. | 604/141 |

Primary Examiner—Sam Rimell
Assistant Examiner—Robert V. Racunas

[57] ABSTRACT

The invention concerns an implantable infusion pump for the dosed administration of medication into the human body, comprising a pump chamber which is formed by a lower chamber part and an upper chamber part connected thereto, whereby the pumping chamber is divided into two subchambers by a gas impermeable flexible partition, the first subchamber is delimited by the upper chamber part and the flexible partition and is designed as a reservoir for medicinal solutions, the upper chamber part has a refilling opening which is sealed by at least one piercable septum and the reservoir for medicinal solutions is connected via an outlet opening and possibly an outlet reduction arrangement with an outlet catheter, and the second subchamber is delimited by the lower chamber part and the flexible partition and is designed as a pressure chamber to accommodate the hexafluorobutane used as a propellant, in particular 1,1,1,4,4,4-hexafluorobutane. The implantable infusion pump according to the invention is without problems from a safety standpoint, has a pumping rate independent of the medication volume, a relatively small temperature gradient, is safe and simple to handle, medication compatible, simple and cost effective to produce and consists of biocompatible material and mutually compatible materials.

2 Claims, 3 Drawing Sheets

IMPLANTABLE INFUSION PUMP

BACKGROUND OF THE INVENTION

1. Field of the Invention

The present invention concerns an implantable infusion pump for the dosed dispensing of medication into the human body.

2. Description of the Prior Art

Implantable infusion pumps are already known. An implantable infusion pump is known from DE 39 15 251 A1 which has a pumping chamber which is formed by a shell-shaped lower part of the chamber and an upper part of the chamber connected thereto. The pumping chamber is divided into two subchambers by means of a flexible membrane. The first subchamber is delimited by the upper chamber part and the membrane and designed as a reservoir for the medication. In the upper part of the chamber a refilling opening which is sealed with a piercable septum is disposed. The septum is jammed between a septum holder connected to the upper part of the chamber and the upper part of the chamber. The medication reservoir is connected with an outlet catheter via an outlet opening and possibly an outlet reduction arrangement. A second subchamber is delimited by the lower part of the chamber and the membrane and designed as a pressure chamber to accommodate a propellant that expands at body temperature.

Infusion pumps with a similar structure are further known from DE 26 04 113 A1 and DE 21 24 062 B2 as well as from DE 4038 049 A1. An additional infusion pump is described in DE 44 32 991 A1 which is hereby expressively referred to for the purpose of disclosure.

The pump components in these infusion pumps are made of biocompatible metal alloys or plastic materials and are connected to each other by means of welding joints or snap-in joints.

Implantable infusion pumps are disposed in a subcutaneous pocket in the area of the abdomen of the patient whereby the refill opening sealed by the septum is palpable under the skin of the patient. The medication reservoir is filled by piercing the skin of the patient and the septum with the corresponding needle of a syringe. Due to the pressure in the syringe, the medication flows through the needle into the medication reservoir.

Implantable infusion pumps are used for the continuous medication (constant dosage) for relatively long periods of time in patients who could otherwise only be treated by injecting the medications, such as, e.g., morphines, heparines and similar drugs, several times daily. Pumps are advantageous in comparison with injections in that the dosage administered no longer has to be given in an overdose so as not to not fall below a certain minimal dosage by the next administration time, but that an even flow and a significantly lower total intake of the drug can be realized. Such infusion pumps, in particular in the case of the administration of pain relievers, are subject to strict safety requirements. Possible over or under dosage must be avoided. Depending on the drug administered, overdosage may result in a high health risk, or, particularly in the case of pain relievers, may even be lethal.

The mode of action in an implantable infusion pump is essentially that the propellant with a boiling point below body temperature contained in the pump partially evaporates subsequent to implantation of the pump into the body of the patient, thus exerting pressure on the drug in the medication reservoir via the separating wall, such as a flexible membrane or a bellows, whereupon the drug flows to the target organ via a reduction system and a catheter. Hereby, the volume of the drug compartment diminishes while the compartment for the propellant increases. The volume increase of the propellant compartment is equalized by the further evaporation of the propellant and takes place at a constant temperature isobar, as long as the propellant provided is a two phase system and no foreign gases exist in the propellant compartment. The isobaric pressure development is necessary for the systems in order to maintain a constant output rate.

Prior art propellants used in implantable infusion pumps do not meet the required specifications. They cause numerous problems.

In DE 40 38 049 A1 the known infusion pump uses 1,2-dichlorotetrafluorethane as a propellant. At body temperature (approx. 37° C.) this propellant develops a pressure of more than 2.5 bar above atmospheric pressure. This pressure must be overcome during the refilling of the medication, a process that is very demanding on the physician in charge of the refilling and very stressful to the patient. Furthermore, this propellant is questionable from a safety standpoint since the walls of the implant are more stressed. A lesser safety problem regarding stress of the implant walls is obtained with Frigen 11. Frigen 11, however, is, like 1,2-dichlorotetrafluorethane, a hydrofluorocarbon (HFC), whose use must be avoided due to its negative effects on the environment (among others, ozone depletion). At body temperature Frigen 11 develops a pressure of only about 0.6 bar above atmospheric pressure and for safety reasons its application would be preferable to 1,2-dichlorotetrafluorethane. If 1,2-dichlorotetrafluorethane is used as a propellant according to DE 40 38 049 A1, the displacement of the infusion pump is less dependent on temperature changes (e.g., fever of the patient) and changes in the counter pressure at the catheter end (e.g., changes in blood pressure, changes in air pressure during travel by airplane or visits in the mountains) than when Frigen 11 is used, for example. However, for the safety reasons mentioned, Frigen 11 still should be preferred over 1,2-dichlorotetrafluorethane.

Further problems result from the previously used propellants due to their relative incompatibility with their surrounding materials such as metals and plastics, in particular plastics.

SUMMARY OF THE INVENTION

The preceding and other shortcomings of prior art methods and systems are overcome by the present invention which provides an implantable infusion pump for the dosed administration of medication into the human body, with a pumping chamber, which is formed by a lower chamber part and an upper chamber part connected thereto, whereby the pumping chamber is divided by a gas impermeable flexible partition into two subchambers, the first subchamber is delimited by the upper chamber part and the flexible partition and designed as a reservoir for medicinal solutions, the upper part of the chamber has a refill opening which is sealed by at least one piercable septum, and the reservoir for medicinal solutions is connected via an outlet opening and possibly an outlet reduction arrangement to an outlet catheter, and the second subchamber is delimited by the lower chamber part and the flexible partition and is designed as a pressure chamber to accommodate a halogenized hydrocarbon propellant, characterized, in that the propellant is hexafluorobutane.

3

The foregoing and additional features and advantages of this invention will become apparent from the detailed description and accompanying drawing figures that follow. In the figures and written description, numerals indicate the various features of the invention, like numerals referring to like features throughout for both the drawing figures and the written description.

DETAILED DESCRIPTION OF THE PREFERRED EMBODIMENTS

The object of this invention is consequently to provide an implantable infusion pump that does not contain any HFC as a propellant, that presents no safety problems, with which a maximum pressure of 2.0 bar is not exceeded in the event of temperature increases due to patient fever (42° C.), the displacement rate is independent of the volume of medication and a relatively small temperature gradient is present, that is safe and simple to handle, is drug compatible, consists of biocompatible material and of mutually compatible materials and can be produced simply and cost effectively.

This object is accomplished with an implantable infusion pump of the type mentioned in the initial description in that according to the invention the propellant hexafluorobutane is used.

Preferably the propellant is 1,1,1,4,4,4-hexafluorobutane.

Figure 1:
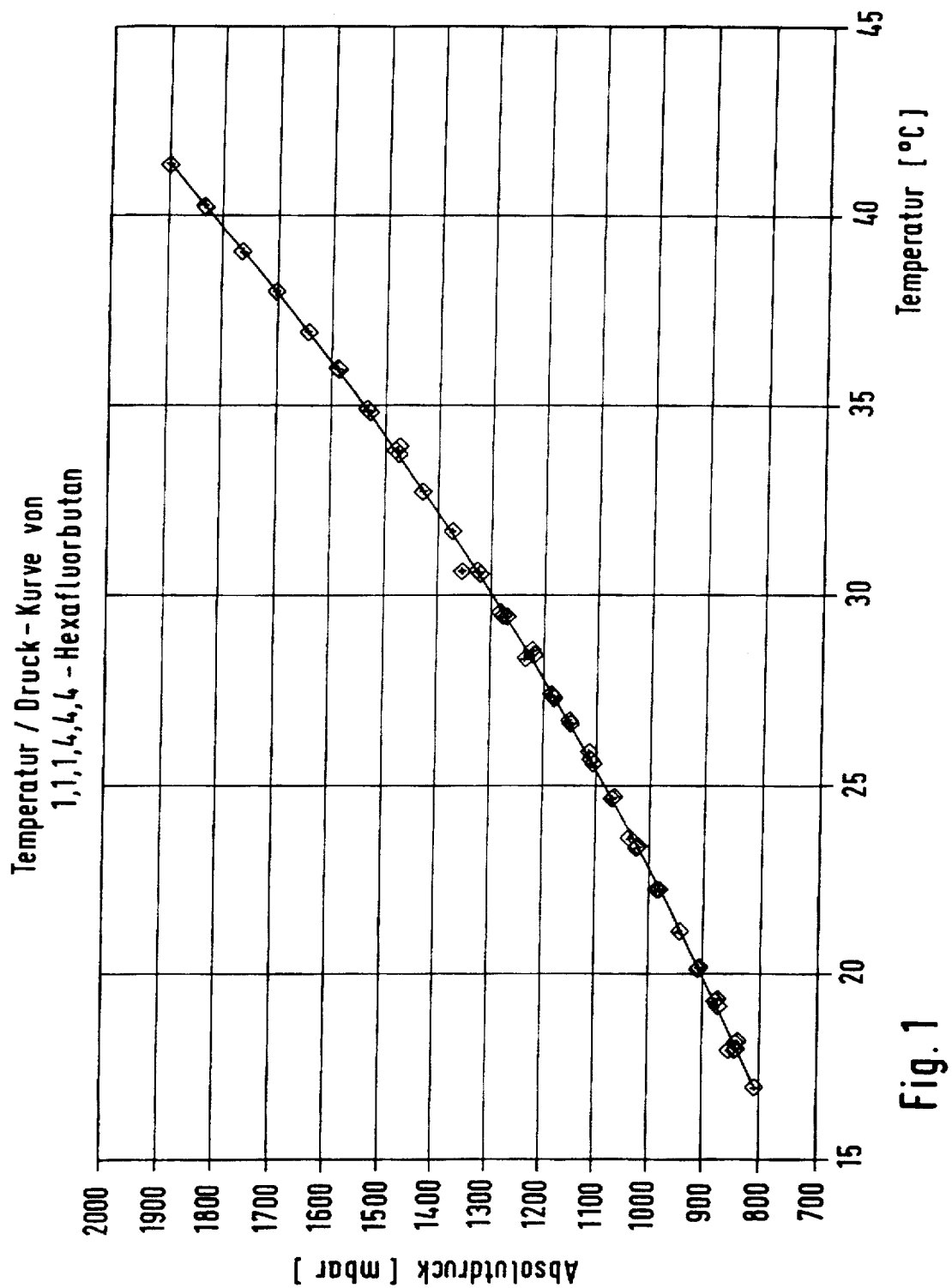
FIG. 1 shows a temperature/pressure curve of 1,1,1,4,4,4-hexafluorobutane (absolute pressure in mbar—temperature in °C.), the propellant used preferably according to the invention.

The propellant used according to the invention has a boiling point of 23° C. It is nontoxic and inert relative to the materials used in the infusion pump, in particular to plastics. The propellant used according to the invention is quite close with regard to its pressure-temperature characteristics to Frigen 11. At body temperature (approx. 37° C.) the propellant develops a pressure of 670 mbar above atmospheric pressure. FIG. 1 attached shows a temperature/pressure curve of the propellant used preferably according to the invention. According to it, a relatively low temperature gradient results for the propellant used according to the invention. The pressure increase with each temperature change of 1° C. is a max. 70 mbar and, specifically is within the range of 55–67 mbar. With regard to these characteristics, the propellant preferably used according to the invention must also be considered harmless from a safety standpoint. There is thus no strong stress on the housing of the infusion pump according to the invention. Furthermore, the refilling of the medication does not require high syringe pressures by the physician entrusted therewith, and stresses for the patient are reduced.

The filling of the pressure chamber with the propellant can take place after removal of the air present from the pressure chamber (e.g., by aspiration) in any suitable manner. It is possible, for example, to introduce a microcapillary through the sealing surface through which the propellant may be filled into the pressure chamber. After the filling with the propellant the capillary can be plugged or withdrawn.

4

The amount of propellant loaded is very small and may amount, for example, to 2 ml, whereas the inner volume of the pressure area may, for example, be 40 ml.

Infusion pumps may be designed in any suitable form and made from any biocompatible material such as metal or plastic. Preferably plastics are used, whereby hard plastics such as polysulphones (incl. polyethersulphones), polyamides and polycarbonates, in particular polysulphones are preferred. The use of infusion pumps made of plastics provides substantial advantages. In addition to lower weight in comparison to infusion pumps made of metal, infusion pumps made of plastics provide the prerequisites for the simultaneous application of certain diagnostic procedures such as thermography and MRI.

In particular, the infusion pumps are designed as they are described in DE 44 32 991 A1 and/or in the patent application simultaneously also submitted with this present patent application under file No. P 195 09 634.7-35 titled "Implantable Infusion Pumps" (under our reference FR2665).

The infusion pump according to the invention is suitable for the continuously dosed administration of medications such as e.g. heparin, artificial pancreatic insulin, chemotherapeutic agents, pain relievers, such as morphine, muscle relaxants, such as baclofen and the like.

The following examples serve to further explain the present invention.

EXAMPLE 1

Figure 2:
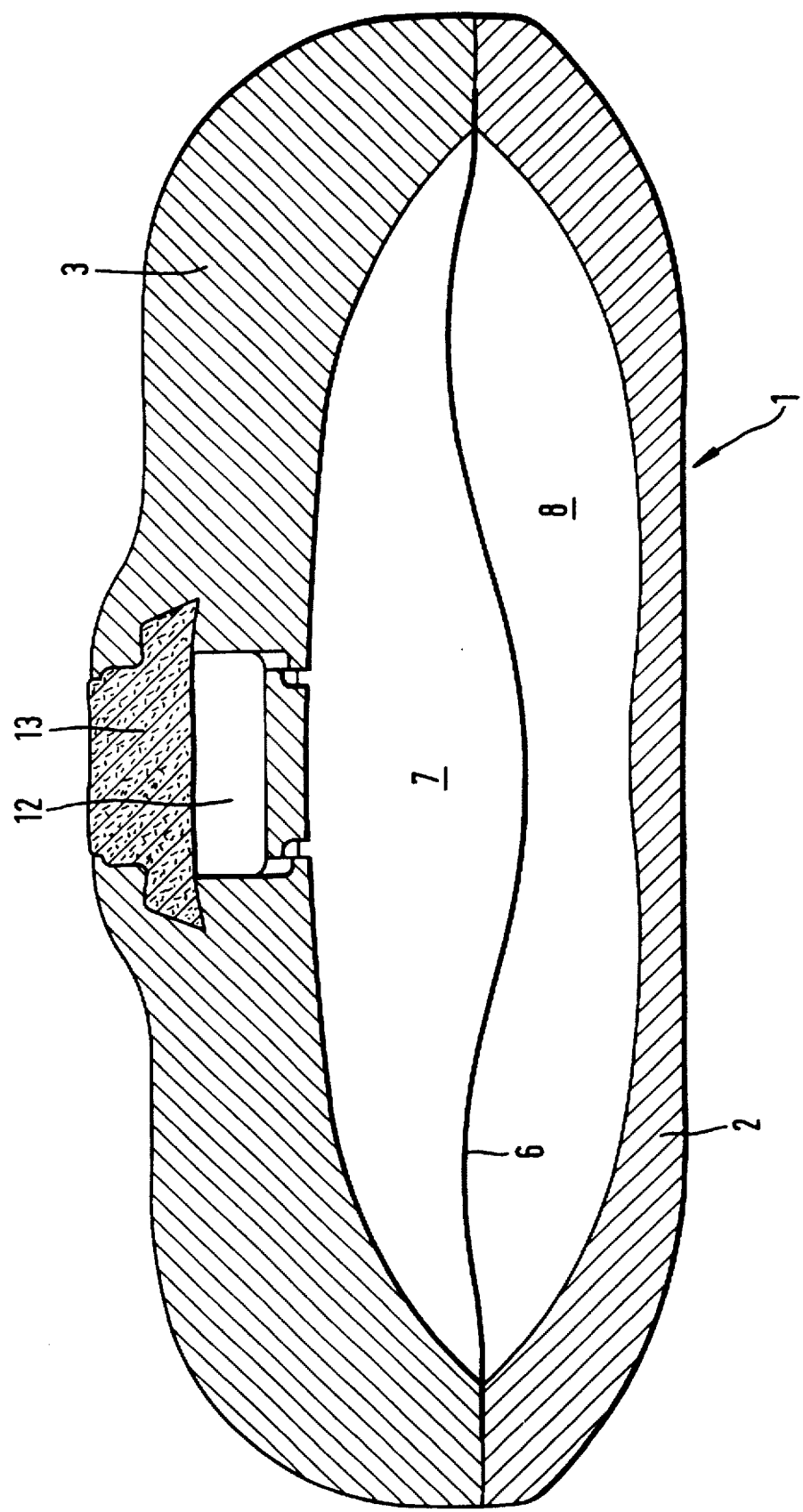
FIG. 2 represents a vertical section through a schematically depicted implantable infusion pump according to the invention.

FIG. 2 represents a vertical section through a schematically depicted implantable infusion pump according to the invention. The infusion pump 1 is a disk-shaped rotationally symmetric body made of hard plastic with a pump chamber which is formed by a lower part of the chamber 2 and an upper part of the chamber 3 and divided by a flexible gas impermeable partition 6 into two subchambers 7 and 9. The first subchamber 7 serves as a medication reservoir and the second subchamber 8 serves as pressure chamber to accommodate the 1,1,1,4,4,4-hexafluorobutane used as a propellant. The refilling opening 12 is covered and sealed by a piercable central septum 13 and has, beneath the central septum 13, a refilling space with a fixed plate serving as a needle stop and passage openings to the medication reservoir 7.

The flexible gas impermeable partition 6 is a flexible membrane as customarily used.

According to an additional preferred embodiment the flexible gas impermeable partition 6 is convex following the contour of the inside of the upper part of the chamber 3 (and corresponding to the lower part of the chamber 2), which was achieved by deep drawing. This partition is stress free. It consists of a film system which, seen from the medication reservoir 7, is composed as follows:

a) film made of polyethyleneterphthalate, thickness 100 µm
b) film made of polychlorotrifluoethylene, thickness 127 µm
c) aluminum composite film made of
   i) polyethyleneterphthalate film, thickness 12 µm
   ii) aluminum foil, thickness 12 µm
   iii) polyethylene film, 70 µm.

The films of the aluminum composite film are joined together by means of a polyurethane adhesive. The films a) and b) are joined together and with the aluminum composite film only in the edge region along the entire circumference. The partition 6 is jammed or pressed between the edge regions of the upper chamber part 3 and the lower chamber part 2 with its outer edge area along its circumference.

The 1,1,1,4,4,4-hexafluorobutane propellant used was brought into the pressure chamber in that a microcapillary was introduced through the sealing surface in the edge area, the air removed from the pressure chamber and subsequently the pressure chamber filled with the propellant through the microcapillary. The amount introduced was approx. 2 ml.

The inner volume of the pressure chamber 8 is approx. 40 ml, and the medication reservoir can accommodate approx. 30 ml of the medicinal solution.

EXAMPLE 2

Figure 3:
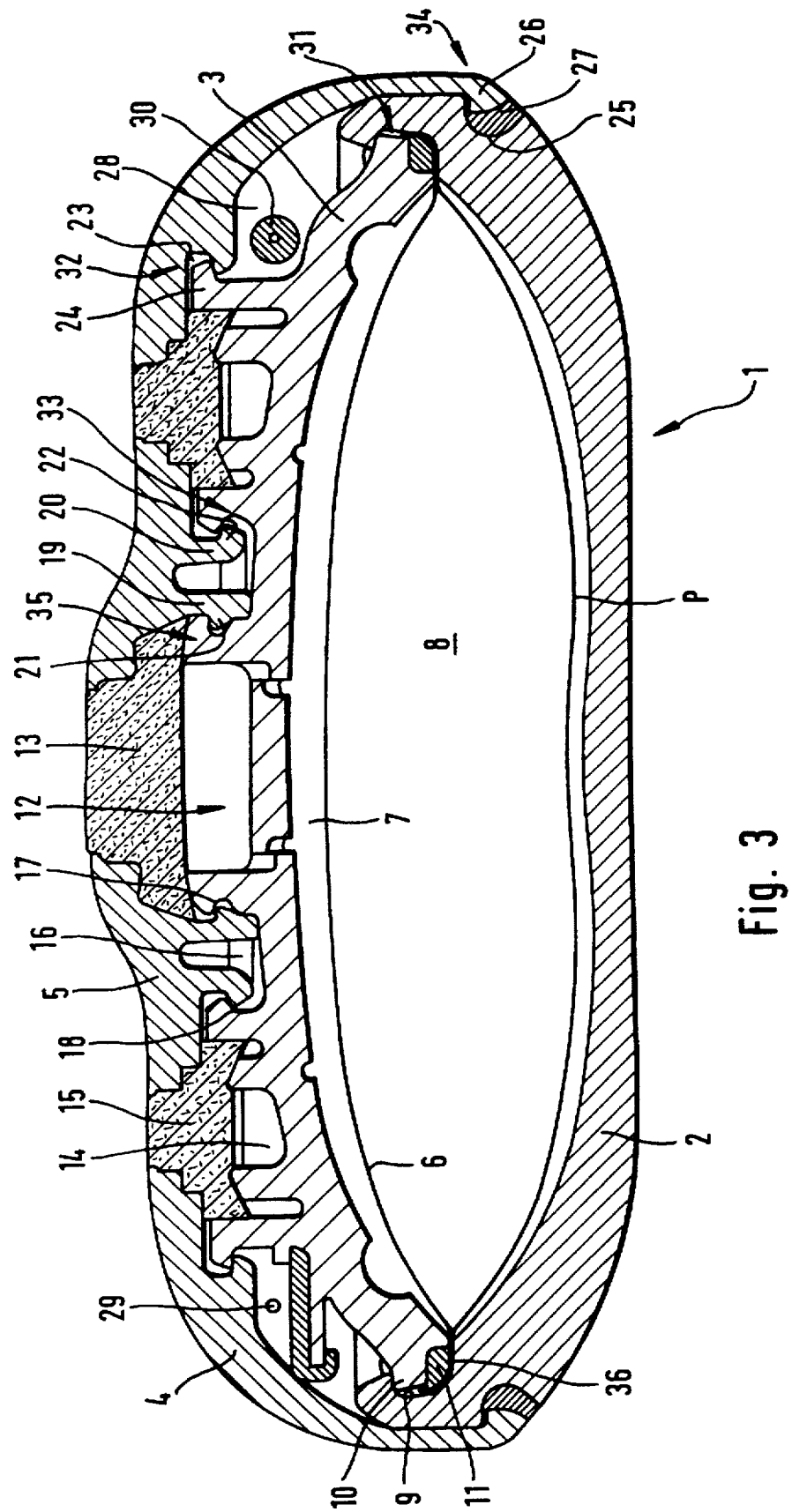
FIG. 3 depicts a vertical section through a specially designed infusion pump for the dosed administration of medications into the human body.

In FIG. 3, a vertical section through a specially designed infusion pump for the dosed administration of medications into the human body is depicted.

The infusions pump 1 is a disk shaped rotationally symmetric body made of polysulphone, with a housing that consists of a shell-shaped lower chamber part 2, a upper chamber part 3 executed in an opposing convex shape, a clasp 4 and a septum holder 5. The inner space is divided by a convex partition 6 and an aluminum composite film P, likewise convex, into a first subchamber serving as a medication reservoir 7 and a second subchamber serving as a pressure chamber 8 to accommodate the 1,1,1,4,4,4-hexafluorobutane used as a propellant. The pressure chamber 8 is formed by welding or glueing the edge of the partition 6 and the aluminum composite film and is shaped in the form of a pill.

At the upper inner edge area of the lower part of the chamber 2 an annular groove is molded, into which, as a snap-in joint, a circumferent corresponding edge 10 of the upper part of the chamber 3 together with an O-ring 11 and one edge 36 formed by the partition 6 and the aluminum composite film P is snapped and sealed.

A refilling opening 12 is sealingly covered by a piercable central septum 13, whereby the refilling opening 12 has a refilling space beneath the central septum 13 with a fixed plate serving as a needle stop and passage openings to the medication reservoir 7.

Furthermore, a concentric annular chamber 14, which is sealingly covered by a ring septum 15, is molded on the upper side of the upper chamber part 3

A concentric annular groove 16 is molded between the annular chamber 14 and the refill opening 12 on the internal and external side walls respectively, a circumferent snapping groove 17, 18 is disposed. The annular shaped septum holder 5 overlaps with its internal edge the edge of the disk shaped central septum 13 and with its external edge the inner edge of the ring of the ring septum 15. Furthermore, the septum holder 5 engages the annular groove 16 together with the adjacent ring webs 19, 20, whereby the latches 21, 22 engage the snapping grooves 17, 18 on the ring webs 19, 20.

The annular outer edge of the ring septum 15 is covered in a stepped arrangement by a correspondingly shaped edge area of the clasp 4 and sealingly jammed against the upper chamber part 3. Furthermore, in this edge area of the clasp 4 a snap-in joint between the clasp 4 and the upper chamber part 3 is provided, which consists of a circumferent snapping groove 23 at the clasp 4 and a circumferent latch 24 at the upper chamber part 3.

At the external side of the edge area of the lower chamber part 2 an additional annular groove 25, in which a circumferent latch 26 engages together with an inserted ring 27, is molded. The latch 26 is the lower edge of the clasp 4 whereby said clasp overlaps the side area of the upper chamber part 3 and the external edge area on the side of the lower chamber part 2 in a bell shape. The clasp 4 is supported (if stressed by high pressure) at the upper chamber part 3 via the latch arrangement 24 and via the annular septum 25 towards the lower chamber part 2.

Between the external wall area of the upper chamber part 3 and an inner wall area of clasp 4 an annular space 28 is formed to accommodate an outlet reduction arrangement 29 (here depicted schematically as a cross-section through a capillary) and an outlet catheter 30.

The connection 31 formed by the annular groove 9, the edge 10 and the O-ring 11, the connection 32 formed by the snapping groove 23 and the latch 24 as well as connection 33 consisting of snapping groove 18 and the latches 22 are the major joints which essentially support the internal pressure stresses occurring from loads from normal operational use.

The connection 34, consisting of the annular groove 25, the latch 26 and the O-ring 27, as well as the connection 35, consisting of the snapping groove 17 and the latches 21, are secondary joints which have no or at least very little support function under normal operational use. The secondary joints 34, 35 provide a support function in the event of a pressure increase above normal operational pressure only, in particular in the case of failure of the primary joints 31, 32, 33.

The primary joints 31, 32, 33 are hereby in constant engagement and ensure the integrity of the implanted infusion pump under normal operational conditions. With an increase of the internal pressure, either in the annular space 28 or in the medication reservoir 7, the secondary joints 34, 35 increasingly engage. Hereby the stresses are transferred from the primary joints 31, 32, 33 and are divided onto primary and secondary joints.

If, for example, the primary joint 31 should fail, the connecting task is taken over by the secondary joint 34. Since simultaneously a gap between the upper chamber part 3 and the lower chamber part 2 occurs, medication escapes into the annular space 28 between the clasp 4 and the upper chamber part 3, thus causing the total pressure and with it the stress of the joint as a whole to decrease. This enables the secondary joint 34 to ensure the integrity of the infusion pump to the outside. It is essential here that the lower part fail in the upper area of the latches but not in the lower part which can be guaranteed by the design.

In case of a failure of the primary joint 32 between the upper part of the chamber 3 and the clasp 4, the connection is also taken over by the secondary joint 34.

Accordingly, in case of a failure or an overload of primary joint 33, a take over or distribution is transferred to the secondary joint 35.

In any case it is advantageous that secondary joints 34, 35 are available in case of an overload or a failure of the primary joints 31, 32, 34, thus guaranteeing a safe continued operation of the infusion pump 1 and therefore substantially improving patient safety.

The partition 6 used in this example corresponds to the partition 6 used in example 1 with regard to its composition as well as its shape. The aluminum composite film P is connected convexly by deep drawing following the contour of the internal wall of the lower part of the chamber 2 and along the edges of the circumference with the partition 6. The aluminum composite film P, seen from the pressure chamber 8, has the following composition:

i) polyethylene film, 70 μm
ii) aluminum foil, thickness 12 μm
iii) polyethyleneterphthalate film, thickness 12 μm The pill shaped pressure chamber 8 thus formed has an inner volume of approx. 40 ml and contains about 2 ml of the propellant. The medication reservoir can accommodate approx. 30 ml of the medicinal solution. The infusion pump according to the invention allows up to a maximum of 120 fillings with the medicinal solution and pumping rates per day of 0.7, 1.0, 1.4, or 2 ml of the medicinal solution, for example.

What is claimed is:

1. An implantable infusion pump for the dosed administration of medication into the human body, comprising a pumping chamber, which is formed by a lower chamber part and an upper chamber part connected thereto, wherein a) the implantable pumping chamber is divided by a gas impermeable flexible partition into two subchambers, b) the first subchamber is delimited by the upper chamber part and the flexible partition and designed as a reservoir for medicinal solutions, the upper part of the chamber has a refill opening which is sealed by at least one piercable septum, and the reservoir for medicinal solutions is connected via an outlet opening to an outlet catheter, and c) the second subchamber is delimited by the lower chamber part and the flexible partition and is designed as a pressure chamber accommodating a halogenized hydrocarbon propellant, wherein the propellant is hexafluorobutane.

2. The infusion pump according to claim 1, wherein the propellant is 1,1,1,4,4,4-hexafluorobutane.

* * * * *

UNITED STATES PATENT AND TRADEMARK OFFICE
CERTIFICATE OF CORRECTION

PATENT NO. : 5,722,957
DATED : March 3, 1998
INVENTOR(S) : Bernd Steinbach

It is certified that error appears in the above-identified patent and that said Letters Patent is hereby corrected as shown below:

Column 2,
Line 26, "hydrofluorocarbon" should read -- chlorofluorocarbon --.
Line 27, "(HFC)" should read -- (CFC) --.

Column 3,
Line 25, "HFC" should read -- CFC --.

Signed and Sealed this

Twentieth Day of September, 2005

JON W. DUDAS
*Director of the United States Patent and Trademark Office*